(12) United States Patent
Eberhardt et al.

(10) Patent No.: US 7,795,466 B2
(45) Date of Patent: Sep. 14, 2010

(54) METHOD FOR PRODUCING SATURATED NITRILES

(75) Inventors: Jan Kurt Eberhardt, Mannheim (DE); Wolfgang Krause, Brühl-Rohrhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 260 days.

(21) Appl. No.: 11/910,295

(22) PCT Filed: Apr. 7, 2006

(86) PCT No.: PCT/EP2006/061431
§ 371 (c)(1),
(2), (4) Date: Oct. 1, 2007

(87) PCT Pub. No.: WO2006/106141
PCT Pub. Date: Oct. 12, 2006

(65) Prior Publication Data
US 2008/0177100 A1 Jul. 24, 2008

(30) Foreign Application Priority Data
Apr. 8, 2005 (DE) .................. 10 2005 016 489

(51) Int. Cl.
*C07C 253/30* (2006.01)
(52) U.S. Cl. .................................................. 558/467

(58) Field of Classification Search .................. 558/467
See application file for complete search history.

(56) References Cited

FOREIGN PATENT DOCUMENTS

JP 2003246769 9/2003
WO WO-2004089879 A1 10/2004

OTHER PUBLICATIONS

Volkova et al. "The synthesis of some nitrogen-containing terpenoid compounds", Maslozhirovaya Promyshelennost, 1983, vol. 4, pp. 26-27.*
Huang et al. "Synthesis, characterization and catalytic properties of palladium-containing electroactive polymers" Synthetic Metals, 1998, vol. 96, pp. 117-122.*
Volkova, O. O., et al., "The synthesis of some nitrogen-containing terpenoid compounds", Maslozhirovaya Promyshelennost, 1983, vol. 4, pp. 26-27, (See Translation).
Profitt, J. A., "A reagent for the α,β reduction of conjugated nitriles", J. Org. Chem., 1976, vol. 40, No. 1, pp. 127-128.

* cited by examiner

*Primary Examiner*—Joseph R Kosack
(74) *Attorney, Agent, or Firm*—Connolly Bove Lodge & Hutz LLP

(57) ABSTRACT

The present invention relates to a process for the preparation of saturated nitrites by catalytic hydrogenation of the corresponding olefinically unsaturated compounds in the presence of a supported transition metal catalyst at a pressure of from 1 to 95 bar. Specifically, the invention relates to a process for the preparation of tetrahydrogeranonitrile (3,7-dimethyloctanenitrile) by catalytic hydrogenation of geranonitrile.

18 Claims, No Drawings

METHOD FOR PRODUCING SATURATED NITRILES

RELATED APPLICATIONS

This application is a national stage application (under 35 U.S.C. 371) of PCT/EP2006/061431 filed Apr. 7, 2006, which claims benefit of German application 10 2005 016 489.7 filed Apr. 8, 2005.

TECHNICAL FIELD OF THE INVENTION

The present invention relates to a process for the preparation of saturated nitrites by catalytic hydrogenation of the corresponding olefinically unsaturated compounds in the presence of a supported transition metal catalyst at a pressure of from 1 to 95 bar. Specifically, the invention relates to a process for the preparation of tetrahydrogeranonitrile (3,7-dimethyloctanenitrile) by catalytic hydrogenation of geranonitrile.

Tetrahydrogeranonitrile (3,7-dimethyloctanenitrile) is an intermediate in industrial organic synthesis. It is used as a fragrance or additive in cosmetics and detergents. Particularly in the case of use as a fragrance, special requirements are placed on the purity of the substance. For example, even small amounts of impurities, specifically of amines, significantly impair the odor impression of the material. In the case of use in cosmetics, moreover, it should be ensured that the tetrahydrogeranonitrile to be used has the fewest possible olefinically unsaturated secondary components or impurities in order to prevent sensitization reactions.

Preparation processes for saturated nitrile compounds by chemoselective hydrogenation of the C—C double bonds which are known are processes such as hydrogenation of geranylnitrile in the presence of modified Raney nickel, as described by O. O. Volkova et al. in Maslozhirovaya Promyshiennnost, 1983, 4, 26-27. In the process, geranonitrile is used as starting material. The unsaturated bond in the α,β position is hydrogenated. Depending on the experimental conditions, the nitrile group is simultaneously reduced to the amine, meaning that this process has a reduced yield of dihydrogeranonitrile. Tetrahydrogeranonitrile is not formed. In addition, the authors also describe the hydrogenation of geranonitrile in the presence of a palladium catalyst supported on activated carbon (5% Pd/C) at a pressure of 100 bar and a temperature of 30° C. The conversion leads to a mixture of tetrahydrogeranonitrile (5%) and the dimer bis(tetrahydrogeranyl)amine (19%).

J. A. Profitt et al. describe in J. Org. Chem. 1975, 40, 127 the hydrogenation of geranylnitrile in the presence of methanol, magnesium and hydrochloric acid. The process permits the selective hydrogenation of the α,β-position C—C double bond and thus produces citronellyinitrile.

WO 2004/089879 discloses a process for the preparation of saturated or unsaturated nitriles which have two to four isoprene units. The compounds mentioned are obtained by selective hydrogenation of the C—C double bond in the α,β position relative to the nitrile function and with the retention of any further C—C double bonds from the corresponding precursor compounds. The hydrogenation is carried out in the presence of amine compounds in an amount of from 0.01 to 100% by weight (based on the nitrite to be converted) and in the presence of a palladium catalyst.

OBJECT OF THE INVENTION

The object of the present invention was to provide a process for the preparation of saturated nitrites, specifically tetrahydrogeranonitrile, by catalytic hydrogenation of the corresponding unsaturated nitrites, specifically geranonitrile, in which it is possible to dispense with the addition of amines and in which the lowest possible amounts of amines and/or olefinically unsaturated compounds are formed as secondary products.

DESCRIPTION OF THE INVENTION AND OF THE PREFERRED EMBODIMENTS

We have found a process for the preparation of saturated nitrites of the formula (I)

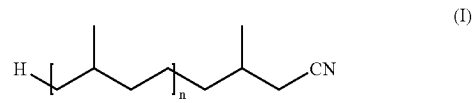

where the index n is an integer from 1 to 3, by converting unsaturated nitrites of the formula (II)

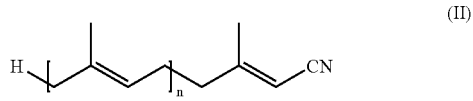

or unsaturated nitrites of the formula (III)

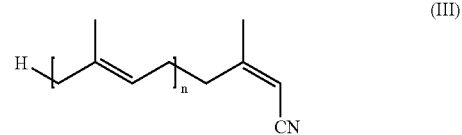

where the index n is in each case an integer from 1 to 3, or by converting mixtures of the unsaturated nitrites of the formulae (II) and (III) in the presence of hydrogen and a supported transition metal catalyst at a pressure of from 1 to 95 bar.

Suitable starting compounds for carrying out the process according to the invention are the compounds of the formulae (II) and (III) which are isomeric with regard to the C—C double bond which is in the α,β position relative to the nitrite function, which can in each case be used as they are or in the form of a mixture with one another. The starting compounds of the formulae (II) and/or (III) in which the index n is 2 or 3 can in each case also be used in the form of isomer mixtures with regard to the C—C double bond or bonds not in the α,β position.

Moreover, suitable starting compounds are also those which are in the form of mixtures with secondary components, it being possible for the secondary components in particular to be those compounds which can be obtained by hydrogenation of one or more C—C double bonds from the compounds of the formulae (II) or (III) or represents the isomers with regard to the position of the C—C double bonds of the specified compounds. By way of example, possible secondary components which may be mentioned for the conversion of geranylnitrile or nerylnitrile to tetrahydrogeranonitrile are: citronellyinitrile and isomers of geranonitrile, such as 3,7-dimethyl-2,7-octadienenitrile, 3,7-dimethyl-3,6-octadienenitrile. The respective secondary components can be present in the unsaturated nitrile to be converted in amounts of in each case about 0.1 to about 25% by weight (based on the total amount of mixture to be converted).

The index n in the formulae (I), (II) and (III) is an integer from 1 to 3. Within the scope of a preferred embodiment of the process according to the invention, n is the number 1 corresponding to a process for the preparation of tetrahydrogeranonitrile of the formula (IV)

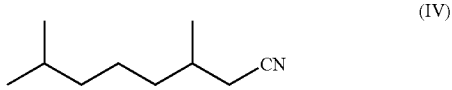

(IV)

by converting geranylnitrile of the formula (V)

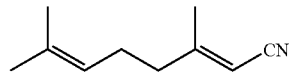

(V)

or nerylnitrile of the formula (VI)

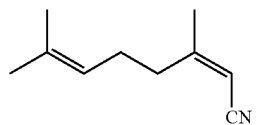

(VI)

or mixtures of geranylnitrile and nerylnitrile.

A starting material which is particularly preferred for the purposes of the present invention is geranonitrile, which is a mixture which consists of approximately equal parts of geranylnitrile of the formula (V) and nerylnitrile of the formula (VI).

The conversion according to the invention is carried out in the presence of hydrogen. The hydrogen can be used in pure form or in the form of mixtures with other, preferably inert, gases, such as, for example, argon and/or nitrogen. Preferably, the reaction is carried out under a hydrogen atmosphere.

The conversion according to the invention is, moreover, carried out in the presence of a supported transition metal catalyst. Transition metal catalysts preferred according to the invention are suspension catalysts, in particular those which comprise, as active components, one or more metals chosen from the group of metals Pd, Ag, Ru, Rh, Ni, preferably Pd. Suitable carrier materials of the catalysts to be used according to the invention are, for example, activated carbon, aluminum oxide, silica gel, $CaCO_3$, $BaSO_4$, $ZrO_2$, $TiO_2$, preferably activated carbon and aluminum oxide and particularly preferably activated carbon.

A catalyst which is particularly preferred for the purposes of the present invention is Pd on activated carbon. The specified catalysts advantageously have metal contents of from about 0.1 to about 20% by weight, preferably from about 0.5 to about 15% by weight and particularly preferably from about 4 to about 11% by weight (in each case based on the reduced metal of the finished catalyst). Such catalysts are commercially available and obtainable, for example, under the names Degussa E1002, Degussa E101, Degussa E105, Degussa E106, Engelhard C3630, Heraeus K201, Heraeus K202, Heraeus K203, Heraeus K204, Heraeus K219.

The chosen catalyst is advantageously used in an amount such that the content of transition metal, preferably Pd, based on the amount of unsaturated nitrile used in each case, for example based on the amount of geranonitrile to be converted, is about 0.00001 to about 1.0% by weight, preferably about 0.0001 to about 0.1% by weight and particularly preferably from about 0.001 to about 0.05% by weight.

According to the invention, the process is carried out at an absolute pressure in the range from 1 to 95 bar. Preferably, the process is carried out at a pressure in the range from about 7 to about 70 bar, particularly preferably in the range from about 10 to about 50 bar.

The process according to the invention is advantageously carried out at temperatures in the range from about 20° C. to about 200° C., preferably in the range from about 35° C. to about 150° C. and particularly preferably in the range from about 50° C. to about 100° C.

The process according to the invention is usually carried out in a suspension procedure in the liquid phase. It can be carried out in the presence of a solvent which is inert under the reaction conditions and is suitable for carrying out hydrogenations, such as, for example, dioxane, tetrahydrofuran, methanol, isopropanol, hexane, or without solvents. Within the scope of a preferred embodiment, in particular for the preparation of tetrahydrogeranonitrile, the process is carried out without the addition of solvent.

The process according to the invention can also be carried out in a mixed liquid/gas phase, with preferably more than 50% by weight of the fluid being in the liquid phase.

The supported catalyst to be used according to the invention can be used successfully in the form of standard commercial supply forms comprising water. Within the scope of a further preferred embodiment of the process according to the invention, the chosen supported catalysts are used in a form which is characterized by the lowest possible water content. Preference is given to using those catalysts, preferably a Pd catalyst supported on activated carbon or aluminum oxide, which have a water content of from 0 to about 70% by weight, particularly preferably from about 0.1 to about 60% by weight, very particularly preferably from about 0.1 to about 50% by weight, especially preferably from about 0.5 to about 30% by weight, even more preferably from about 0.5 to about 10% by weight and most preferably from about 0.5 to about from such 5% by weight. Such catalysts are commercially available or can be made available through processes known per se to the person skilled in the art, for example through predrying.

The process according to the invention can be successfully carried out without the addition of promoters or auxiliaries. In this connection, for the purposes of the present invention, promoters or auxiliaries are understood as meaning, for example, amine compounds, specifically aliphatic or aromatic organic amines, such as, for example, trimethylamine, triethylamine, tri-n-butylamine, tri-n-octylamine, diethylamine, diisopropylamine, di-n-butylamine, di-sec-butylamine, n-butylamine, sec-butylamine, tert-butylamine, n-octylamine, triethanolamine, diethanolamine, ethanolamine, N,N,N',N'-tetramethylethylenediamine, 3-methoxypropylamine, 3-ethoxypropylamine, 3-(methylamino)propylamine, 3-(dimethylamino)propylamine, 3-(dibutylamino) propylamine, morpholine, 1,4-diazabicyclo[2.2.2]octane, 1,5-diazabicyclo[4.3.0]nonene-5 and 1,8-diazabicyclo[5.4.0]undecene-7, pyridine, N,N-dimethylaminopyridine, and quinoline. Promoters are also understood as meaning dopings of the catalyst used in each case, examples of doping metals being zinc, cadmium, silver, copper and manganese. Consequently, the abovementioned commercially available catalysts are suitable for use for the purpose of the process according to the invention without further modifications or additives.

According to the invention, preference is given to processes for the preparation of tetrahydrogeranonitrile of the formula (IV) by catalytic hydrogenation of geranylnitrile, nerylnitrile or mixtures thereof or preferably of geranonitrile in the presence of a supported palladium catalyst, the hydrogenation being carried out without the addition of amine compounds. The conversion is carried out within the scope of a further preferred embodiment at a temperature of from about 20° C. to 200° C. and a pressure of from about 1 to about 95 bar, particularly preferably at a temperature of from about 35° C. to about 150° C. and a pressure of from about 7 to about 70 bar and is most preferably carried out at a temperature of from about 50° C. to about 100° C. and a pressure of from about 10 to about 50 bar.

Of suitability for carrying out the process according to the invention are the reactors known to the person skilled in the art and appearing suitable for carrying out hydrogenations in the suspension procedure, such as, for example, stirred autoclaves or packed bubble columns.

The process according to the invention can be carried out discontinuously, semicontinuously or completely continuously.

Depending on the reaction conditions chosen, the conversion according to the invention has usually largely finished after about 1 to about 24 h, often after about 12 h. In the customary way, the crude reaction mixture is separated from the catalyst used, freed from the solvent used if appropriate and, if desired, further purified or separated by suitable methods, for example by distillation.

The process according to the invention opens up an economically efficient and technically advantageous access to saturated nitriles, in particular to tetrahydrogeranonitrile. The latter is characterized by a low content of aminic secondary components and impurities, as a result of which further purification for producing tetrahydrogeranonitrile in fragrance quality is often not required.

EXAMPLES

The examples below serve to illustrate the invention without limiting it in any way:

The experiments in Examples 1 to 16 and also in the comparative example were carried out in the laboratory in a 300 ml stirred autoclave, the experiments in Examples 17 and 18 were carried out in a pilot-plant autoclave with 9 liter volume. Geranonitrile and the particular catalyst were initially introduced into the autoclave. The autoclave was flushed with nitrogen and hydrogen was injected in. The reaction mixture was then heated to the reaction temperature. The stirrer speed was 1000 rpm in the laboratory experiment, and the speed in the pilot-plant experiment (Examples 17 and 18) was 600 rpm.

The reaction products were analyzed by means of gas chromatography (separating column DBWAX, length 30 m; internal diameter 0.32 mm; carrier gas nitrogen; temperature program: 80° C., then heating to 230° C. at around 3° C./min, finally 10 min isotherm at 230° C.). Conversions, yields and selectivities are given below on the basis of GC area percentages.

Example 1

100 g of technical-grade geranonitrile (content 97.7%) and 2 g of a catalyst comprising 5% by weight of Pd on activated carbon with a water content of 53% by weight (corresponding to 0.05% by weight of Pd with regard to geranonitrile) were initially introduced. The hydrogenation was carried out at a hydrogen pressure of from 15 to 29 bar and a reaction temperature of from 25 to 31° C. After a reaction time of 18 h, a geranonitrile conversion of 95.1% at a product selectivity with regard to tetrahydrogeranonitrile of 75.4% was achieved. The predominant secondary component found was partially hydrogenated geranylamine (dihydrogeranylamine) in an amount of 14.9%.

Example 2

100 g of technical-grade geranonitrile (content 97.7%) and 1 g of a catalyst comprising 5% by weight of Pd on activated carbon with a water content of 3% by weight (corresponding to 0.05% by weight of Pd with regard to geranonitrile) were initially introduced. The hydrogenation was carried out at a hydrogen pressure of from 12 to 28 bar and a reaction temperature of initially 25° C. The temperature increased in the course of the reaction to 63° C. After a reaction time of 315 min, a geranonitrile conversion of 99.7% at a product selectivity with regard to tetrahydrogeranonitrile of 99.8% was achieved.

Example 3

100 g of technical-grade geranonitrile (content 97.7%) and 0.5 g of a catalyst comprising 5% by weight of Pd on activated carbon with a water content of 3% by weight (corresponding to 0.025% by weight of Pd with regard to geranonitrile) were initially introduced. The hydrogenation was carried out at a hydrogen pressure of from 8 to 29 bar and a reaction temperature of initially 50° C. The temperature increased in the course of the reaction to 69° C. After a reaction time of 220 min, the heating was stopped. The reaction mixture was stirred for a further 14 h at a hydrogen pressure of 20 bar. The pressure in the autoclave was then released. The geranonitrile conversion was 98.4%, the selectivity with regard to tetrahydrogeranonitrile was 99.6%.

Example 4

100 g of technical-grade geranonitrile (content 97.7%) and 0.1 g of a catalyst comprising 5% by weight of Pd on activated carbon with a water content of 3% by weight (corresponding to 0.005% by weight of Pd with regard to geranonitrile) were initially introduced. The hydrogenation was carried out at a hydrogen pressure of from 9 to 31 bar and a reaction temperature of 60° C. After a reaction time of 330 min, the heating was stopped. The reaction mixture was stirred for a further 14 h at a hydrogen pressure of 29 bar. A geranonitrile conversion of 69.7% was ascertained. The selectivity with regard to tetrahydrogeranonitrile was 83.5%.

The reaction product was converted for a further 240 minutes at a hydrogen pressure of from 11 to 29 bar and a reaction temperature of 100° C. The conversion increased to 95.4% with a selectivity with regard to tetrahydrogeranonitrile of 97.1%.

Example 5

100 g of technical-grade geranonitrile (content 97.7%) and 1.0 g of a catalyst comprising 5% by weight of Pd on activated carbon with a water content of 3% by weight (corresponding to 0.005% by weight of Pd) were initially introduced. The hydrogenation was carried out at a hydrogen pressure of from 5 to 30 bar and a reaction temperature of 80° C. After a reaction time of 240 min, a content of 99.7% (GC area percent) of tetrahydrogeranonitrile were ascertained.

The reaction product was removed from the reactor and filtered to separate off the catalyst. The catalyst was transferred to the autoclave with geranonitrile and used for further geranonitrile hydrogenations under the same reaction conditions. In the second reaction run, after a reaction time of 240 min at 80° C. and a hydrogen pressure of from 5 to 30 bar, a tetrahydrogeranonitrile content of again 99.7% was reached. In the third reaction run, after reaction for 4 hours under the same conditions, a tetrahydrogeranonitrile content of 99.4% was achieved.

Example 6

100 g of technical-grade geranonitrile (content 97.7%) and 1.0 g of a catalyst comprising 10% by weight of Pd on activated carbon with a water content of about 5% by weight (Degussa E101 N/D, corresponding to 0.01% by weight of Pd with regard to geranonitrile) were initially introduced. The hydrogenation was carried out at a hydrogen pressure of from 6 to 29 bar and a reaction temperature of initially 50° C. The temperature increased in the course of the reaction to 70° C. After a reaction time of 240 min, the heating was stopped. The reaction mixture was stirred for a further 14 h at a hydrogen pressure of 26 bar. The reaction mixture was then stirred for a further 240 min at 60° C. and a hydrogen pressure of 25 bar. The geranonitrile conversion was 99.1%, the selectivity with regard to tetrahydrogeranonitrile was 99.7%.

Example 7

100 g of technical-grade geranonitrile (content 97.7%) and 1.0 g of a catalyst comprising 5% by weight of Pd on activated carbon with a water content of 3% by weight (corresponding to 0.05% by weight of Pd with regard to geranonitrile) were initially introduced. The hydrogenation was carried out at a hydrogen pressure of from 4 to 30 bar and a reaction temperature of 150° C. After a reaction time of 45 min, a geranonitrile conversion of 99.9% was ascertained. The tetrahydrogeranonitrile content was 99.3%.

Example 8

150 g of geranonitrile (content 98.9%) and 1.5 g of a catalyst comprising 5% by weight of Pd on activated carbon with a water content of 3% by weight (corresponding to 0.05% by weight of Pd with regard to geranonitrile) were initially introduced. The hydrogenation was carried out at a hydrogen pressure of 30 bar and a reaction temperature of 75° C. After a reaction time of 330 min, a geranonitrile conversion of more than 99.9% was ascertained. The tetrahydrogeranonitrile content of the product was 96.4%. The predominant secondary component detected was the tertiary amine tris(3,7-dimethyloctyl)amine in an amount of 3.2%.

Example 9

150 g of geranonitrile (content 98.9%) and 3.0 g of a catalyst comprising 5% by weight of Pd on activated carbon with a water content of 53% by weight (corresponding to 0.05% by weight of Pd with regard to geranonitrile) were initially introduced. The hydrogenation was carried out at a hydrogen pressure of 30 bar and a reaction temperature of 80° C. After a reaction time of 360 min, a geranonitrile conversion of more than 99.9% was ascertained. The tetrahydrogeranonitrile content of the product was 84.9%. The content of the tertiary amine tris(3,7-dimethyloctyl)amine was 13.9%.

Example 10

150 g of technical-grade geranonitrile (content 97.7%) and 3.0 g of a catalyst comprising 5% by weight of Pd on activated carbon with a water content of 53% by weight (corresponding to 0.05% by weight of Pd with regard to geranonitrile) were initially introduced. The hydrogenation was carried out at a hydrogen pressure of 30 bar and a reaction temperature of 75° C. After a reaction time of 360 min, a geranonitrile conversion of more than 99.9% was ascertained. The tetrahydrogeranonitrile content was 96.3%. As secondary component, 2.2% of the tertiary amine tris(3,7-dimethyloctyl)amine were detected.

Example 11

150 g of geranonitrile (content 98.9%) and 3.0 g of a catalyst comprising 5% by weight of Pd on activated carbon with a water content of 50% by weight (corresponding to 0.05% by weight of Pd with regard to geranonitrile) were initially introduced. The hydrogenation was carried out at a hydrogen pressure of 30 bar and a reaction temperature of 75° C. After a reaction time of 270 min, a geranonitrile conversion of more than 99.9% was ascertained. The tetrahydrogeranonitrile content was 84.7%. The content of tertiary amine tris(3,7-dimethyloctyl)amine was 14.1%.

Example 12

150 g of technical-grade geranonitrile (content 97.7%) and 3.0 g of a catalyst comprising 5% by weight of Pd on activated carbon with a water content of 53% by weight (corresponding to 0.05% by weight of Pd with regard to geranonitrile) were initially introduced. The hydrogenation was carried out at a hydrogen pressure of 5 bar and a reaction temperature of 50° C. After a reaction time of 320 min, a geranonitrile conversion of 99.4% was ascertained. The tetrahydrogeranonitrile content in the reaction product was 71.9%, the fraction of tris(3,7-dimethyloctyl)amine was 0.3%. Citronellyinitrile was detected with a content of 19.8%.

Example 13

150 g of geranonitrile (content 98.9%) and 0.1 g of a catalyst comprising 5% by weight of Pd on activated carbon with a water content of 53% by weight, corresponding to 0.0017% by weight of Pd with regard to geranonitrile) were initially introduced. The hydrogenation was carried out at a hydrogen pressure of 50 bar and a reaction temperature of 60 to 77° C. After a reaction time of 290 min, a geranonitrile conversion of 99.0% was ascertained. The tetrahydrogeranonitrile content in the reaction product was 71.9%, the fraction of tris(3,7-dimethyloctyl)amine was 0.2%. Citronellyinitrile was detected with a content of 25.0%.

Example 14

150 g of geranonitrile (content 98.9%) and 1.5 g of a catalyst comprising 5% by weight of Pd on activated carbon with a water content of 53% by weight, corresponding to 0.025% by weight of Pd with regard to geranonitrile) were initially introduced. The hydrogenation was carried out at a hydrogen pressure of 5 bar and a reaction temperature of from 70 to 81° C. After a reaction time of 360 min, a geranonitrile conversion of more than 99.9% was ascertained. The tetrahydrogeranonitrile content in the reaction product was 84.5%, the fraction of tris(3,7-dimethyloctyl)amine was 0.6%. Citronellyinitrile was detected with a content of 13.7%.

Example 15

100 g of geranonitrile (content 98.9%) and 0.2 g of a catalyst comprising 5% by weight of Pd on activated carbon with a water content of 53% by weight, corresponding to 0.005% by weight of Pd with regard to geranonitrile) were initially introduced. The hydrogenation was carried out at a hydrogen pressure of 20 bar and a reaction temperature of from 144 to 162° C. After a reaction time of 240 min, a geranonitrile conversion of more than 99.9% was ascertained. The tetrahydrogeranonitrile content in the reaction product was 98.1%, the fraction of tris(3,7-dimethyloctyl)amine was 0.8%.

Example 16

150 g of geranonitrile (content 98.9%) and 1.5 g of a catalyst comprising 5% by weight of Pd on activated carbon with a water content of 53% by weight (corresponding to 0.025% by weight of Pd with regard to geranonitrile) were initially introduced. The hydrogenation was carried out at a hydrogen pressure of from 70 bar and a reaction temperature of from 85 to 102° C. After a reaction time of 240 min, a geranonitrile conversion of 99.7% was ascertained. The tetrahydrogeranonitrile content in the reaction product was 96.5%, the fraction of tris(3,7-dimethyloctyl)amine was 2.4%.

Example 17

5200 g of technical-grade geranonitrile (content 97.7%) and 31.2 g of a catalyst comprising 5% by weight of Pd on activated carbon with a water content of about 50% by weight (corresponding to 0.015% by weight of Pd with regard to geranonitrile) were initially introduced. The hydrogenation was started at a hydrogen pressure of 10 bar and a reaction temperature of 60° C. After a reaction time of 60 minutes, the reaction temperature was increased to 80° C. in steps of 5° C. every 60 minutes. After the reaction temperature of 80° C. had been reached, the reaction pressure was increased to 20 bar over the course of 2 h. After a reaction time of a further 5 hours, the hydrogen pressure was increased to 30 bar over the course of 1 h. After a reaction time of a further 5 hours, the reaction temperature was increased from 80 to 100° C. over the course of 1 hour. Finally, the reaction was run for a further 5 hours at 100° C. and 30 bar.

After a reaction time of 16 h in total, a geranonitrile conversion of more than 99.9% with a product selectivity with regard to tetrahydrogeranonitrile of 99.8% was achieved. The only secondary component detected was tris(3,7-dimethyloctyl)amine in an amount of 0.2%. The product composition did not change in the remaining reaction time.

Example 18

5200 g of technical-grade geranonitrile (content 97.7%) and the catalyst recovered from Example 17 were initially introduced. The hydrogenation was carried out under the same reaction conditions as in Example 17. The activity of the reused catalyst was slightly worse than in Example 17. After a reaction time of 16 h, a geranonitrile conversion of more than 99.9% was ascertained, the tetrahydrogeranonitrile content was 96.8%, the fraction of dihydrogeranonitrile was 3.0%. After a reaction time of 21 h in total, a geranonitrile conversion of more than 99.9% with a product selectivity with regard to tetrahydrogeranonitrile of 99.8% was achieved. Tris(3,7-dimethylocty)amine was detected as secondary component in an amount of 0.2%.

Comparative Example 150 g of geranonitrile (content 98.9%) and 4.5 g of Raney nickel were initially introduced. The hydrogenation was carried out at a hydrogen pressure of from 10 to 15 bar and a reaction temperature of 40° C. After a reaction time of 330 min, a geranonitrile conversion of 19.2% was ascertained. The tetrahydrogeranonitrile content was 0.3%. The content of dihydrogeranonitrile (citronellyinitrile) was 16.4%.

The reaction was continued for a further 390 min at a hydrogen pressure of 30 bar and a reaction temperature of 50° C. The geranonitrile conversion improved to 48.9%. The tetrahydrogeranonitrile content in the reaction product was 0.5%, the content of dihydrogeranonitrile was 43.2%.

We claim:

1. A process for the preparation of saturated nitriles of the formula (I)

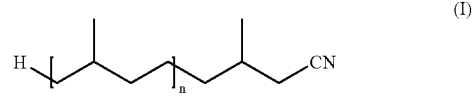

where the index n is an integer from 1 to 3,
which comprises converting unsaturated nitriles of the formula (II)

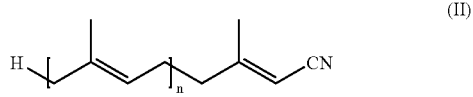

or unsaturated nitriles of the formula (III)

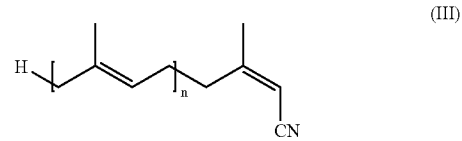

where the index n is in each case an integer from 1 to 3,
or by converting mixtures of the unsaturated nitriles of the formulae (II) and (III) in the presence of hydrogen and a Pd catalyst supported on activated carbon or aluminum oxide, which have a water content of from about 3 to about 60% by weight at a pressure of from 1 to 95 bar.

2. The process according to claim 1 for the preparation of tetrahydrogeranonitrile of the formula (IV)

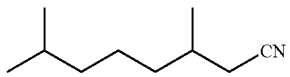 (IV)

by converting geranylnitrile of the formula (V)

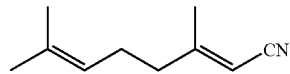 (V)

or nerylnitrile of the formula (VI)

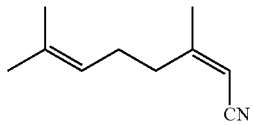 (VI)

or mixtures of geranylnitrile and nerylnitrile.

3. The process according to claim 1, wherein the conversion is carried out at a pressure of from 7 to 70 bar.

4. The process according to claim 1, wherein the conversion is carried out at a pressure of from 10 to 50 bar.

5. The process according to claim 1, wherein the conversion is carried out at a temperature of from 20° C. to 200° C.

6. The process according to claim 1, wherein the conversion is carried out at a temperature of 50° C. to 100° C.

7. The process according to claim 1, wherein the Pd catalyst is supported on activated carbon.

8. The process according to claim 1, wherein the Pd catalyst is supported on aluminum oxide.

9. The process according to claim 1, wherein the catalyst has a water content of up to 10% by weight.

10. The process according to claim 1, wherein the catalyst is used in an amount such that the content of Pd, based on the amount of nitrile to be converted, is 0.00001 to 1.0% by weight.

11. The process according to claim 1, wherein the catalyst is used in an amount such that the content of Pd, based on the amount of nitrile to be converted, is 0.001 to 0.05% by weight.

12. The process according to claim 1, wherein the conversion is carried out without the addition of promoters or auxiliaries.

13. The process according to claim 1, wherein the conversion is carried out without the addition of amine compounds.

14. The process according to claim 2, wherein geranylnitrile or nerylnitrile or mixtures of geranylnitrile and nerylnitrile are used in the form of mixtures with one or more secondary components, the secondary components being selected from the group consisting of citronellylnitrile, 3,7-dimethyl-2,7-octadienenitrile and 3,7-dimethyl-3,6-octadienenitrile and are present in an amount, based on the total amount of mixture to be converted, of in each case 0.1 to 25% by weight.

15. The process according to claim 1, wherein the water content is from about 3 to about 50% by weight.

16. The process according to claim 1, wherein the water content is from about 3 to about 30% by weight.

17. The process according to claim 1, wherein the water content is from about 3 to about 10% by weight.

18. The process according to claim 1, wherein the water content is from about 3 to 5% by weight.

* * * * *